United States Patent [19]

Fearnot

[11] Patent Number: 5,040,533
[45] Date of Patent: Aug. 20, 1991

[54] IMPLANTABLE CARDIOVASCULAR TREATMENT DEVICE CONTAINER FOR SENSING A PHYSIOLOGICAL PARAMETER

[75] Inventor: Neal E. Fearnot, West Lafayette, Ind.

[73] Assignee: Medical Engineering and Development Institute Incorporated, West Lafayette, Ind.

[21] Appl. No.: 458,599

[22] Filed: Dec. 29, 1989

[51] Int. Cl.$^5$ ............................................... A61N 1/00
[52] U.S. Cl. ............................... 128/419 PG; 128/637
[58] Field of Search ........ 128/419 PG, 419 P, 419 D, 128/634, 637

[56] References Cited

U.S. PATENT DOCUMENTS

| | | | |
|---|---|---|---|
| 4,722,342 | 2/1988 | Amundson | 128/419 PG |
| 4,763,655 | 8/1988 | Wirtzfeld et al. | 128/419 PG |
| 4,846,195 | 7/1989 | Alt | 128/419 PG |
| 4,886,064 | 12/1989 | Strandberg | 128/419 PG |
| 4,896,068 | 1/1990 | Nilsson | 128/419 PG |

Primary Examiner—Francis Jaworski
Assistant Examiner—George Manuel
Attorney, Agent, or Firm—Richard J. Godlewski

[57] ABSTRACT

An implantable container for housing a cardiovascular treatment device is disclosed with a window positioned in an external wall thereof for sensing a physiological parameter for the treatment device. The window is formed of an insulating material such as glass, a semiconductor material, or a membrane for sensing any one of a plurality of various physiological parameters. In one embodiment, the window material is glass on which a pair of electroptic devices are positioned on the interior surface thereof for emitting and receiving optical signals for sensing the physiological parameter. In another embodiment, the window comprises glass with a plurality of electrodes externally positioned thereon for measuring, for example, the electrical properties of the physiological parameter. In yet another embodiment of the window, the window material comprises a semiconductor material having a plurality of layers formed therein to form an ion selective field effect transistor for measuring concentrations of various fluids coming in contact therewith. In another embodiment, the semiconductor material forms a thermistor for sensing thermal properties of the physiological parameter. In yet another embodiment, the window comprises a membrane through which mechanical vibrations or pressures of surrounding tissue or fluids are sensed.

20 Claims, 4 Drawing Sheets

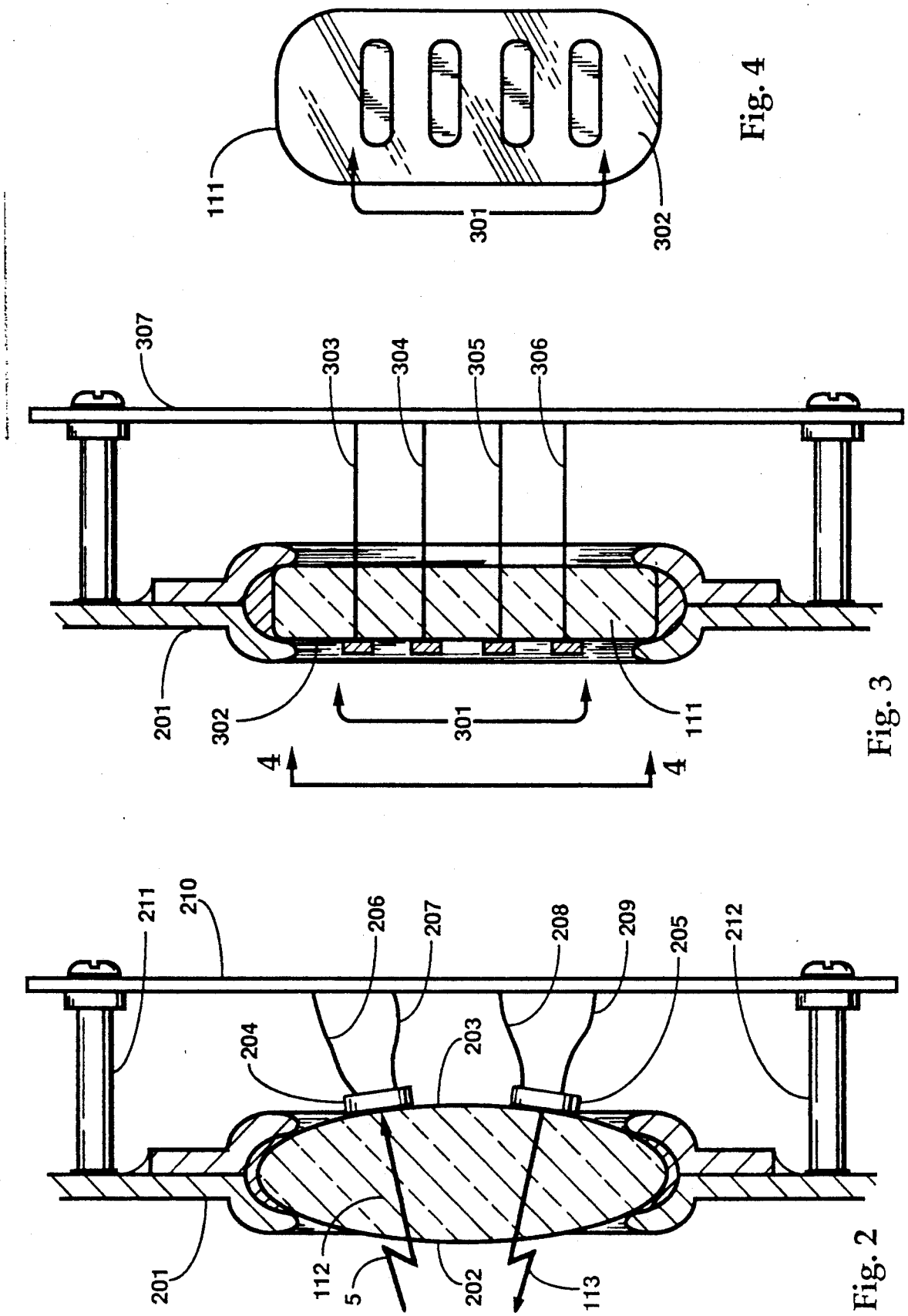

IMPLANTABLE CARDIOVASCULAR TREATMENT DEVICE CONTAINER FOR SENSING A PHYSIOLOGICAL PARAMETER

TECHNICAL FIELD

This invention relates to cardiovascular treatment devices and particularly to a container of such devices for sensing a physiological parameter.

BACKGROUND OF THE INVENTION

The human body is equipped to adapt to the varying needs of chemical and electrical stimulants during everyday activity including exercise. If the heart is functioning properly, the nervous system increases the heart rate through electrical stimulation and reduces peripheral resistance in response to exercise. Similarly, the endocrine glands regulate production of chemical hormones to meet the varying demands of the body during everyday activity. However, a large, increasing population of patients have implantable devices to compensate for various heart conduction disorders. With rate adaptive and exercise-responsive pacemakers being developed, the pacemaker has not only become a life-sustaining device for a significant number of people with cardiac conduction problems, but it has also become a device for improving the quality of life for these patients to lead a more normal existence. In addition, cardiovascular treatment devices such as implantable defibrillators and medication dispensers are available for providing treatment in emergency and other situations.

Several physiological parameters have been utilized to administer cardiovascular treatment. These parameters include, amongst others, nerve electrical activity, biochemical concentrations such as enzymes and glucose, blood pressure, blood and body temperature, oxygen saturation, metal ion concentration (pH), respiration, motion, etc. Among other uses, physiological parameters have been utilized to indicate pacing rates during exercise including pH, QT interval, respiratory rate, body motion, and the venous blood temperature in the right ventricle of the heart.

From the original fixed-rate cardiac pacemaker evolved the demand pacemaker. The demand pacemaker ceases to produce an electrical stimulus when a spontaneous heart beat is detected. The presence of a spontaneous heart beat is indicated by a normal QRS complex in the electrocardiogram. In addition to sensing the presence of electrical activity in the ventricle, sensing of atrial activity has also been used. In an attempt to provide sensing information, the nerves leading to the heart, in particular the sympathetic nerves, will provide information processed by the brain that naturally increases the heart rate. Unfortunately, current technology prohibits the use of a long-term nerve impulse transducer.

The pH of the blood has also been measured and used to control the rate of a cardiac pacemaker. However, pH transducers that are implantable for long periods of time are difficult to produce and therefore are not yet in common use.

In another prior art cardiac pacemaker, ambient body temperature is measured by a charging capacitor having a high temperature coefficient located within the pulse generator circuitry. However, since ambient body temperature does not vary appropriately as a function of muscle exertion, this device will not respond to a body's need for increased cardiac output due to muscular exertion.

In still yet another cardiac pacemaker, the nonambient blood temperature in the right ventricle of the heart along with the sensing of body motion are utilized to control the stimulation of the heart.

In yet another prior art cardiac pacer, the respiratory rate is used to vary the production of electronic pulses which are fed to a constant current source connected to the ventricle of the heart.

In still another cardiac pacemaker, the oxygen saturation of the blood is measured as a control variable for influencing the frequency of stimulation. Light conductor probes implanted in the heart determine the blood oxygen saturation therein.

In a programmable tachycardia pacer, dual functions of demand pacing as well as standby tachycardia breakup are performed. A command parameter control circuit is used for programmably controlling the parameters of the pacer operation as well as of the tachycardia recognition and response.

In a self-contained artificial heart, the pulse rate and the stroke rate vary in response to blood pressure. Variations in blood pressure are detected by means of a pressure sensitive transistor, thereby varying the rate of pumping of blood in response to blood pressure.

As indicated from the above-described cardiovascular treatment devices, any number of physiological parameters may be utilized for providing electrical stimulation or chemical treatment of the patient. Often, sensors for each of these physiological parameters are implanted within the patient to indicate a particular measure or level of the physiological parameter to control the stimulation rate or treatment of the patient.

With respect to sensing nonambient venous blood temperature as disclosed in U.S. Pat. Nos. 4,436,092 and 4,543,954 of the present inventor, a thermistor along with pacing electrodes are positioned within the right ventricle of the heart for sensing the nonambient temperature of blood returning to the right ventricle of the heart. A separate lead extending from the pacemaker housing connects to the thermistor for sensing the nonambient blood temperature. The resistance of the thermistor varies as the temperature of the blood changes, thereby indicating changes in the exercise level of the patient. The changes in resistance of the thermistor are externally sensed and fed back to the control circuit of the pacemaker positioned within the pacemaker housing.

Similarly, a photoemitter and detector are positioned along with the pacing leads in the right ventricle of the heart to sense changes in oxygen saturation of the blood. Changes in the reflectance or density of the optical signal emitted from the photoemitter are sensed by the photodetector to indicate the level of oxygen saturation in the right ventricle of the heart.

In addition, pressure transducers are also positioned in the heart along with the pacing leads to indicate a measure or level of blood pressure changes for indicating stimulation rates.

A problem associated with all of these sensors is that they are placed external to the pacemaker container along with the electrical conductors leading thereto for sensing the physiological parameter. At a minimum, such sensors increase the bulk and complexity of the pacemaker lead leading to the heart. Sensors positioned external to the pacemaker housing and heart also present additional problems of fixation and migration. This is particularly true with respect to measuring respiratory rate or parameters associated with respiration.

Another problem with these externally placed sensors is the increased risk of failure and subsequent surgical intervention. Surgical intervention to remove and replace these externally positioned sensors involves lifethreatening risks and associated medical expense

SUMMARY OF THE INVENTION

The foregoing problems are solved and a technical advance is achieved with an illustrative implantable cardiovascular treatment device container having a window therein for sensing a physiological parameter. The container includes an enclosure for housing a cardiovascular treatment device and a window included in an external wall of the enclosure for sensing the physiological parameter. In one illustrative embodiment, the container is utilized for a cardiac pacemaker for variably controlling the stimulation rate of the heart according to a measure of the physiological parameter. Included in the cardiac pacemaker is a sensor unit responsive to the physiological parameter for producing a signal indicative of the measure of the physiological parameter such as the temperature or oxygen saturation of blood. In one variation, the sensor unit includes an output circuit for producing an output signal indicative of the level of the sensed physiological parameter.

The pacemaker further includes a stimulator unit such as a pulse generator responsive to a rate control signal for applying an electrical stimulus to the heart and a control unit responsive to the sensor signal for generating a rate control signal according to a predetermined algorithm relating the stimulation rate to the measure of the physiological parameter. In this embodiment, the container houses the sensor, control, and stimulator units therein. The sensor unit is advantageously positioned adjacent the window provided in the external wall of the container for sensing the physiological parameter.

In this embodiment of the cardiac pacemaker, the sensor unit includes a photoemitter and a photodetector utilizing optical signals for sensing the physiological parameter. As a result, the window of the container includes a transparent material for passing the optical signals therethrough.

In another embodiment, the window includes an electrically insulating material and a plurality of electrodes positioned thereon for indicating a measure or for sensing the level of an electrical property such as the impedance of the physiological parameter.

In still another embodiment, the window advantageously includes a semiconductor material for indicating a measure or for sensing a level of a physiological parameter such as a concentration of either metallic ions, enzymes, or glucose.

In yet another embodiment, the window comprises a membrane for indicating a measure or for sensing the level of a physiological parameter such as blood pressure, respiratory volume, or body motion. A further example of the container window includes thermally conductive means for measuring a thermal property of the physiological parameter. Alternatively, the window advantageously includes electrically conductive means for measuring ion concentrations of the parameter. Combinations of sensors included with the window indicate a measure or sense a level of any one of a number of different physiological parameters.

Advantageously, the inclusion of a window within an external wall of the implantable cardiovascular treatment device container eliminates the need for external leads and the accompanying problems associated therewith. The sensor unit is advantageously placed within the sealed container for sensing the parameter either with or through the window of the container.

BRIEF DESCRIPTION OF THE DRAWING

FIG. 2 depicts a partial cross-sectional view of the external wall of the container and window of FIG. 1;

FIG. 3 depicts an alternative illustrative embodiment of the window of FIG. 1 with electrodes positioned on the outer surface thereof;

FIG. 4 depicts the external surface of the window of FIG. 3 with horizontally positioned electrodes thereon;

DETAILED DESCRIPTION

Figure 1:
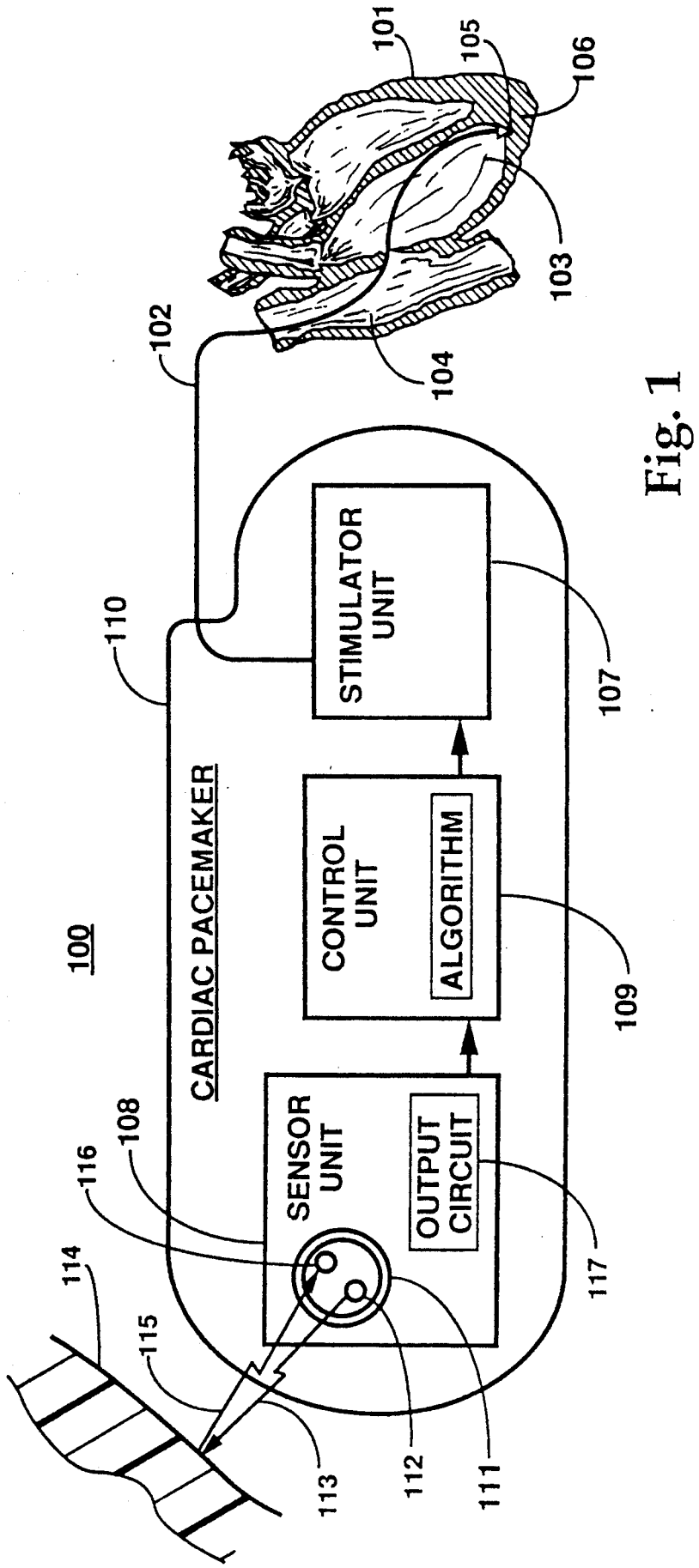
FIG. 1 is an illustrative diagram of an implantable cardiovascular treatment device of which is housed in a container having a window for sensing a physiological parameter.

Depicted in FIG. 1 is a diagram of an illustrative implantable cardiovascular treatment device such as a rate-adaptive cardiac pacemaker 100 which is housed in container 110 having a window 111 in an external wall thereof for sensing a physiological parameter therethrough. Based on the physiological parameter sensed through the window of the implanted container, the pacemaker stimulates heart 101 of a patient (not shown) via heart pacemaker lead 102. The pacemaker lead is surgically implanted subcutaneously in a well-known manner in the right ventricle 103 of the heart via superior vena cava 104. At the distal end, the pacemaker lead includes pacing electrode 105, which is implanted at the apex 106 of the right ventricle. The pacemaker lead conducts an electrical signal from a stimulator unit such as a well-known pulse generator circuit 107 of the pacemaker to the pacing electrode and heart. The electrical signal stimulates the heart at a predetermined stimulation rate determined by the cardiac pacemaker. The cardiac pacemaker variably controls the stimulation rate of the heart according to a measure or a sensed level of the physiological parameter, such as the oxygen saturation of the blood, which is measured through the container window from tissue or fluid 114 that is adjacent the window.

In addition to pulse generator circuit 107, cardiac pacemaker 100 basically includes sensor unit 108 and control unit 109. The sensor unit is responsive to the physiological parameter for producing an output signal indicative of the measure of the oxygen saturation of the blood or for sensing a level of the blood oxygen saturation. By way of example, the sensor unit includes a pair of well-known electroptic devices such as photoemitter 112 and photodetector 116 for sensing the level of the oxygen saturation of the blood via optical signals 113 and 115, respectively. In addition, the sensor unit also includes a well-known output circuit 117 for producing an output signal indicative of the level of the sensed parameter.

Control unit 109 is responsive to this output signal from the sensor unit for generating a rate control signal according to a predetermined algorithm relating the stimulation rate to the measure or level of the oxygen saturation of the blood. Disclosed in U.S. Pat. No. 4,202,339 to Wirtzfeld is a description of a cardiac pacemaker that measures the oxygen saturation of the blood as a control variable for influencing the frequency of stimulation. A description of the relationship or algorithm between the oxygen saturation of blood and the stimulation rate of the heart is also included therein. Descriptions of an algorithm relating the nonambient temperature of the blood in the right ventricle of the heart to the stimulation rate of the heart are disclosed in U.S. Pat. Nos. 4,436,092 and 4,543,954 of the present inventor.

The well-known pulse generator circuit of stimulator unit 107 is responsive to the rate control signal from the control unit for electrically stimulating the heart at a stimulation rate determined by the control unit algorithm. The pacemaker also includes container 110 for hermetically containing the sensor, control, and stimulator units therein. The container also includes window 111 in the external wall thereof in which a sensor is included or is closely positioned thereby for sensing the physiological parameter.

Pacemaker container 110 is a well-known housing and is comprised of a biocompatible material such as titanium, stainless steel, tantalum, or other alloys. The pacemaker circuitry is hermetically sealed in the container housing through which the pacemaker lead is connected through a well-known electrical connector.

Depicted in FIG. 2 is a partial cross-sectional view of external wall 201 and window 111 of pacemaker container 110. Window 111 is mechanically affixed in a well-known manner in or at the external wall of the container as shown. In this particular illustrative embodiment, the window comprises a transparent material such as glass for transmitting an optical signal therethrough. As shown, glass window 111 is shaped with double convex surfaces 202 and 203. Affixed in a well-known manner to internal convex surface 203 is photodetector 204 and photoemitter 205. Photoemitter 205 emits optical signal 113 therefrom through the glass window to blood flowing in adjacent tissue when the pacemaker is implanted in the patient. The pacemaker is surgically implanted in a pocket formed near the right or left clavicle with the pacemaker lead being inserted through the right or left subclavian vein to the right ventricle of the heart. When the container is implanted in the patient, optical signal 113 from photoemitter 205 is incident on blood flowing by window 111. The blood reflects the incident optical signal as reflected optical signal 115 to the photodetector 204. The intensity of this reflected optical signal is dependent on the level of the oxygen saturation of the blood.

Electrical signals to and from the pair of electroptic devices are provided by a plurality of electrical conductors 206–209. The conductors are terminated on circuit board 210 positioned within the container via well-known standoffs 211 and 212 for positioning the circuit board as well as any other circuitry or units within the pacemaker container.

Depicted in FIG. 3 is a partial cross-sectional view of external wall 201 of the container with an alternative embodiment of window 111. In this second embodiment, the window comprises an electrically insulating material such as glass with a plurality of electrodes 301 positioned in a well-known manner on or in the external surface 302 of the glass material. Conductors 303–306 pass through the insulating material from the plurality of electrodes to circuit board 307 positioned adjacent the internal surface of the window.

Depicted in FIG. 4 is a front view of external surface 302 of window 111 with electrodes 301 positioned in a horizontal manner. This horizontal or parallel electrode orientation is preferred for obtaining localized electrical measurements of, for example, fluid or tissue positioned next to or adjacent the window.

Figure 5:
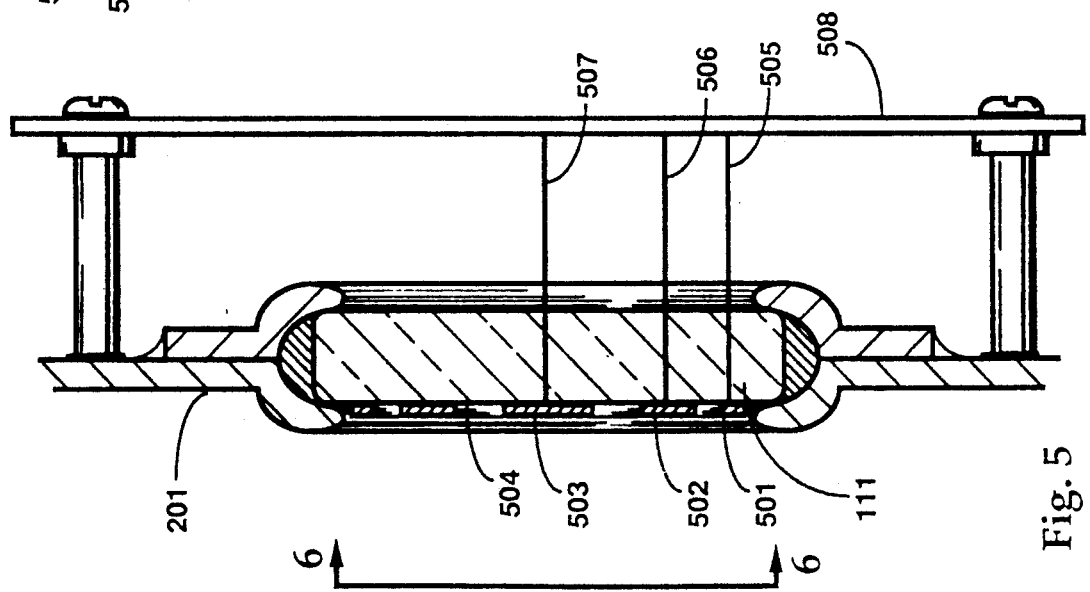
FIG. 5 depicts a second alternative illustrative embodiment of the window of FIG. 1 with electrodes concentrically positioned on the outer surface thereof.

Depicted in FIG. 5 is a partial cross-sectional view of external wall 201 of the container with a second alternative embodiment of window 111. In this third embodiment, the window again comprises an electrically insulating material such as glass with a plurality of electrodes 501–503 concentrically positioned in a well-known manner on or in the external surface 504 of the glass material. Conductors 505–507 pass through the insulating material from the electrodes to circuit board 508 positioned adjacent the internal surface of the window.

Figure 6:
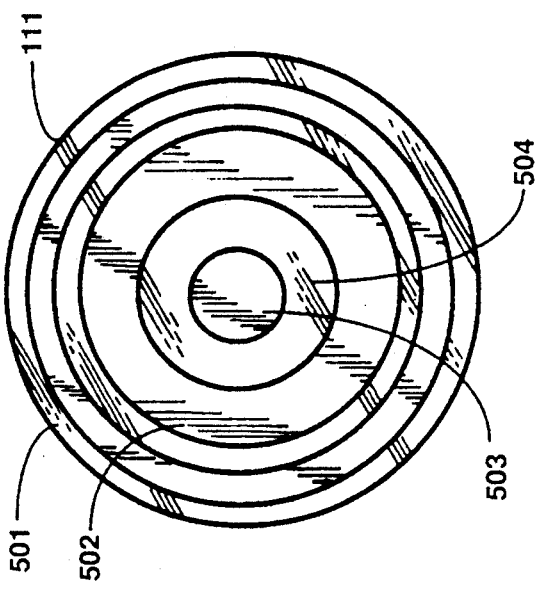
FIG. 6 depicts the external surface of the window of FIG. 5 with concentrically positioned electrodes thereon.

Depicted in FIG. 6 is a front view of external surface 504 of window 111 with electrodes 501–503 positioned thereon in a concentric manner for measuring the electrical properties over a larger sensing field. This configuration is particularly useful when measuring the physiological parameter associated with respiration. With either of the electrode configurations of FIGS. 4 or 6, the electrodes are utilized to measure or sense an electrical property such as the impedance of a fluid or tissue within the sensing field of the electrodes.

Figure 7:
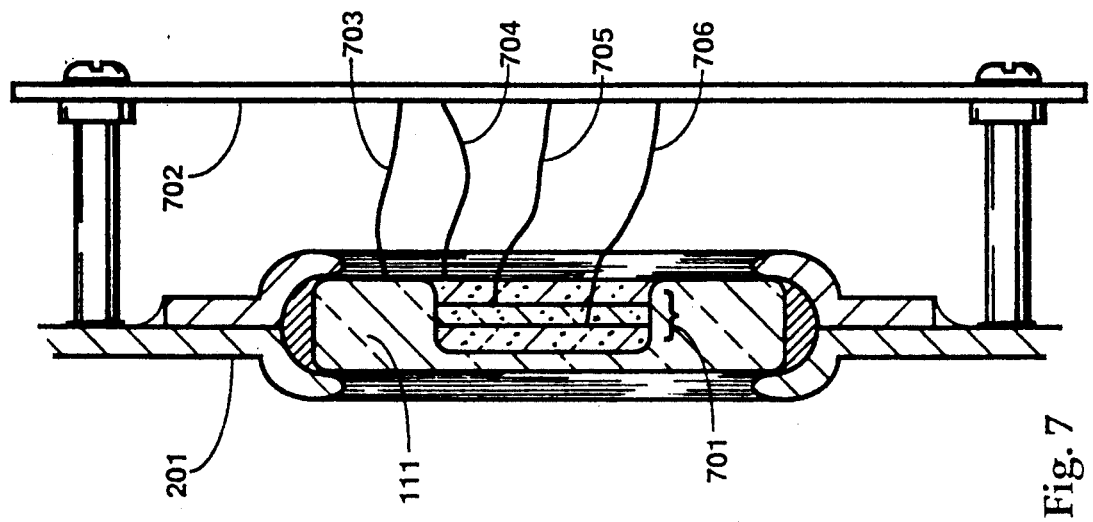
FIG. 7 depicts a third alternative illustrative embodiment of the window of FIG. 1.

Depicted in FIG. 7 is a partial cross-sectional view of external container wall 201 with a third alternative embodiment of window 111. In this fourth embodiment, the window comprises a well-known semiconductor material such as silicon. This semiconductor material has a plurality of doped layers 701 positioned therein for transmitting an output signal indicative of a measure or sensed level of the physiological parameter to circuit board 702 via conductors 703–707. Alternatively, the semiconductor material may be formed and electrically stimulated to transmit an output signal to a receiver positioned external to the container. By way of example, the semiconductor material and layers 701 may be fabricated to form a well-known ion selective field effect transistor. One form of the ion selective field effect transistor is the chemical field effect transistor for measuring chemical concentrations of fluids passing on the surface of the window. The ion selective field effect transistor may be also utilized for sensing enzymes, glucose concentrations, and other chemical properties which effect the conductive property of the semiconductor material. The semiconductor material may also be fabricated with a plurality of layers to form a thermistor for measuring the thermal properties of the surrounding tissue or fluid. Furthermore, in another embodiment of the semiconductor material, the plurality of layers are arranged to form a charge coupled device, which is sensitive to optical intensities of light reflected from the surrounding tissue or fluid.

Figure 8:
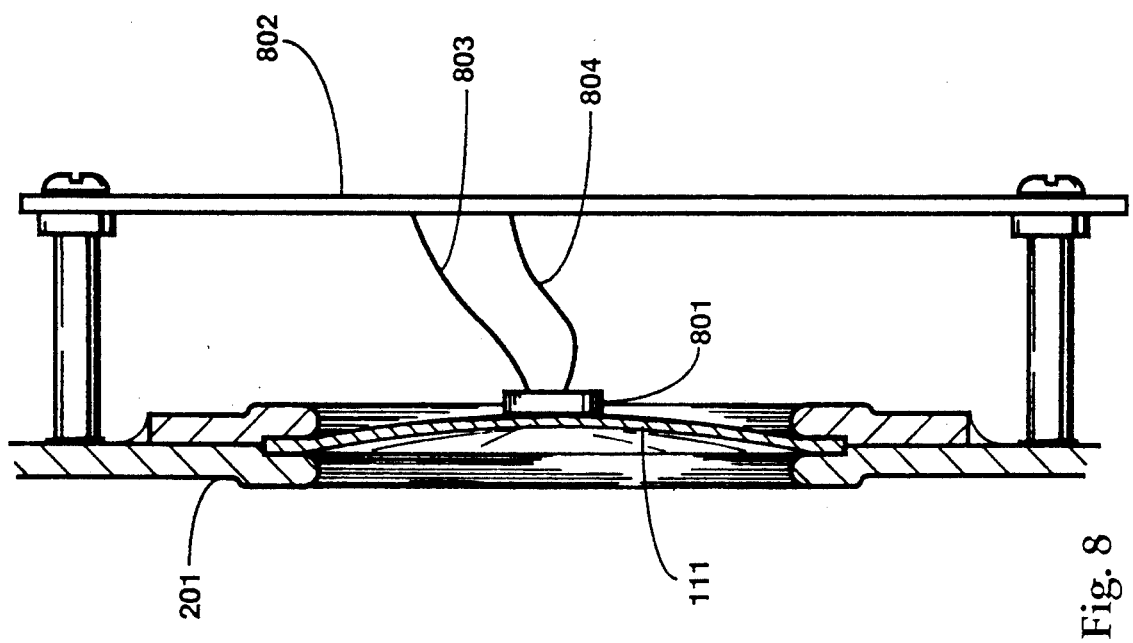
FIG. 8 depicts a fourth alternative illustrative embodiment of the window of FIG. 1.

Depicted in FIG. 8 is partial cross-sectional view of external wall 201 with a fourth alternative embodiment of window 111. In this fifth embodiment, the window comprises a well-known flexible membrane for sensing one of several different kinds of physiological parameters such as pressure, minute volume, or body motion. Adjacent to the internal surface of the membrane wall is circuit board 802 for terminating sensor conductors 803 and 804 from sensor 801. In one embodiment, sensor 801 comprises a well-known motion sensor such as a piezoelectric crystal for sensing pressure and movement of the membrane due to the presence of fluid or tissue on the external surface of the membrane. In another embodiment, sensor 801 comprises an ultrasonic transducer for sending and receiving ultrasonic signals to the surrounding tissue through the membrane.

It is to be understood that the above-described implantable cardiovascular treatment device container for sensing a physiological parameter is merely an illustrative embodiment of the principles of this invention and that other apparatus may be devised by those skilled in the art without departing from the spirit and scope of this invention. In particular, the window formed in an external wall of the device container is utilized for sensing any physiological parameter which may be brought in contact or in proximity to the window. A sensor may be positioned internal to the device container for sensing through the window. The window itself may also be constructed to form the sensor. Although described as a cardiac pacemaker, the implantable cardiovascular treatment device container may also be utilized for such treatment devices such as a defibrillator or medication release device for providing life support and medication at prescribed threshold levels sensed by the treatment device.

I claim:

1. A cardiac pacemaker for variably controlling a stimulation rate of a heart according to a measure of a physiological parameter, comprising:
    a sensor unit responsive to said physiological parameter and capable of producing a first signal indicative of the measure of said physiological parameter;
    a stimulator unit responsive to a rate control signal and capable of stimulating said heart;
    a control unit responsive to said first signal and capable of generating said rate control signal according to a predetermined algorithm relating the stimulation rate to the measure of said physiological parameter; and
    a container housing at least said sensor unit and said control unit, said container having an external wall including a window positioned therein, said sensor unit being positioned about said window for sensing said physiological parameter in cooperation with said window.

2. The pacemaker of claim 1 wherein said sensor unit includes a photodetector capable of receiving through said window a first optical signal indicative of the measure of said physiological parameter.

3. The pacemaker of claim 2 wherein said sensor unit further includes a photoemitter capable of emitting through said window a second optical signal for indicating the measure of said physiological parameter.

4. The pacemaker of claim 1 wherein said sensor unit comprises an electrode positioned about said window and capable of indicating a measure of said physiological parameter.

5. The pacemaker of claim 1 wherein said window comprises a semiconductor material forming said sensor unit.

6. The pacemaker of claim 1 wherein said window comprises a membrane.

7. A cardiac pacemaker for variably controlling the stimulation rate of a heart according to a level of a physiological parameter, comprising:
    sensor means for sensing a physiological parameter, said parameter being related by an algorithm to the heart rate in a normally functioning heart, said sensor means including output means for producing an output signal indicative of the level of said sensed physiological parameter;
    control means responsive to said output signal for implementing said algorithm;
    stimulator means connected to said control means and responsive thereto for variably controlling the stimulation rate of said heart;
    container means for housing at least said sensor means and said control means in a sealed environment, said container means having an external wall including window means positioned therein for sensing said physiological parameter in cooperation with said sensor means.

8. The pacemaker of claim 7 wherein said container means further includes means for positioning said sensor means proximate to said window means.

9. The pacemaker of claim 7 wherein said window means includes a transparent material.

10. The pacemaker of claim 7 wherein said window means includes electrode means for sensing an electric property of said physiological parameter.

11. The pacemaker of claim 7 wherein said window means includes membrane means for sensing the level of said physiological parameter.

12. The pacemaker of claim 7 wherein said window means comprises semiconductor means for sensing.

13. The pacemaker of claim 7 wherein said window means includes thermally conductive means for sensing a thermal property of said physiological parameter.

14. The pacemaker of claim 7 wherein said window means includes electrically conductive means for sensing an ion concentration of said physiological parameter.

15. An implantable cardiovascular treatment device container for sensing a physiological parameter, comprising
    an external enclosure having an external wall and capable of housing a cardiovascular treatment device circuit, and
    said external wall including a window positioned therein, said window being capable of sensing said physiological parameter.

16. The container of claim 15 wherein said window includes an electrical conductor for sensing said parameter.

17. The container of claim 15 wherein said window includes a semiconductor material capable of sensing said physiological parameter.

18. The container of claim 15 wherein said window includes a membrane capable of sensing said physiological parameter.

19. The container of claim 15 further comprising a photodetector positioned on said window capable of receiving a first optical signal indicative of said physiological parameter and wherein said window includes a transparent material capable of passing said optical signal therethrough.

20. The container of claim 19 further comprising a photoemitter capable of emitting through said transparent material a second optical signal means for sensing said physiological parameter.

* * * * *